United States Patent [19]
Kuo et al.

[11] Patent Number: 5,783,605
[45] Date of Patent: Jul. 21, 1998

[54] HELPER INDUCERS FOR DIFFERENTIATION THERAPY AND CHEMOPREVENTION OF CANCER

[76] Inventors: Sheng-Chu Kuo, 5F-1, 19, Lane 238, Ssu-Ping Road; Jau-Hong Lee, 7F-5, 229, Ching-Tao Road, Section 3, both of Taichung, Taiwan

[21] Appl. No.: 730,737

[22] Filed: Oct. 15, 1996

Related U.S. Application Data

[63] Continuation of Ser. No. 398,304, Feb. 27, 1995, abandoned.

[51] Int. Cl.$^6$ .................................................. A61K 31/19
[52] U.S. Cl. .................. 514/629; 514/415; 514/418; 514/419; 514/544; 514/570
[58] Field of Search ................................ 514/629, 415, 514/418, 419, 570, 544

[56] References Cited

U.S. PATENT DOCUMENTS 4,470,970  9/1984  Burzynski ............................. 424/177

FOREIGN PATENT DOCUMENTS

93/07866  4/1993  WIPO ..................................... 514/629

OTHER PUBLICATIONS

Burzynski S. R. et al., "Preclinical Studies on Antineoplaston AS2–1 and Antineoplaston AS2–5", Drugs Exptl. Clin. Res., Suppl. 1, XII, 11–16 (1986).

Burzynski S. R., "Toxicology Studies on Antineoplaston AS2–5 Injections in Cancer Patients", Drugs Exptl. Clin. Res., Suppl. 1, XII, 17–24 (1986).

Burzynski S. R. et al., "Toxicology Studies on Antineoplaston AS2–1 Injections in Cancer Patients", Drugs Exptl. Clin. Res., Suppl. 1, XII, 25–35 (1986).

Burzynski S. R. et al., "Preclinical Studies on Antineoplaston A10 Injections", Drugs Exptl. Clin. Res., Suppl. 1, XII, 37–45 (1986).

Burzynski S. R. et al., "Toxicology Studies on Antineoplaston A10 Injections in Cancer Patients", Drugs Exptl. Clin. Res., Suppl. 1, XII, 47–55 (1986).

Burzynski S. R. et al., "Initial Clinical Studies with Antineoplaston A2 Injections in Cancer Patients with Five Years Follow–up", Drugs Exptl. Clin. Res., Suppl. 1, XIII, 1–12 (1987).

Chemical Abstracts 111:169028, "Urinary Metabolites of N,N–diethylphenylacetamide", Rao et al., Jan. 1989.

Chemical Abstracts 90:168323, "N–alkylcarboxylic acid amides", S. Linke, Feb. 1979.

*Primary Examiner*—Frederick Krass
*Attorney, Agent, or Firm*—Hitt Chwang & Gaines, PC

[57] ABSTRACT

Cancer cells are blocked from entering differentiation pathways because of abnormal methylation enzymes, which are responsible for keeping cancer cells in cycling state. Effective differentiation inducers are those capable of acting directly or indirectly to convert abnormal methylation enzymes into normal enzymes, thereby enabling cancer cells to undergo terminal differentiation. Differentiation employing inducer alone often can not reach completion because of the damage created by the inducer. Such damage can be prevented if differentiation is induced in the presence of helper inducers, which are basically inhibitors of the component enzymes of methylation. Thus, differentiation induced in the presence of helper inducers is more likely to reach completion. Therefore, helper inducers are essential components of differentiation therapy, not just merely to potentiate the activity of differentiation inducers. The present inventors discover that alkyl phenylacetamides, alkyl phenylacetate, 2,4-dichlorophenylacetate, and indole acetate are potent helper inducers.

2 Claims, 8 Drawing Sheets

HELPER INDUCERS FOR DIFFERENTIATION THERAPY AND CHEMOPREVENTION OF CANCER

This is a continuation application of U.S. application Ser. No. 08/398,304, filed Feb. 27, 1995, now abandoned.

FIELD OF THE INVENTION

The present invention relates to differentiation therapy and chemoprevention of cancer, and in particular to novel helper inducers which act on abnormal methylation enzymes of cancer cells.

BACKGROUND OF THE INVENTION

Abbreviations used are:
AdoHcy: s-adenosyl homocysteine
AdoMet: s-adenosyl methionine
MAT: methionine adenosyltransferase
MT: methyltransferase
NBT: nitroblue tetrazolium
RA: retinoic acid
SAHH: s-adenosyl homocysteine hydrolase Differentiation therapy of cancer Differentiation therapy may be the most ideal therapy for cancers if target cancer cells have ample receptors for inducers to initiate biological responses. The therapeutic efficacy is excellent and adverse side effects are minimal. Interferon and retinoic acid have produced remarkable results in the treatment of hairy cell leukemia (1), and acute promyelocytic leukemia (2,3), respectively, that these differentiation inducers are considered to be the drugs of choice for the treatment of these cancers. The success of differentiation therapy is, however, rather limited. After all differentiation therapy is just on the horizon. Many problems associated with this therapy still remain to be solved. At the moment, the immediate difficulties are that cancers responding well to interferon therapy are only a few, and the remission resulting from retinoic acid therapy is very short. Besides, mechanisms of differentiation therapy are not yet well established.

Role of methylation enzymes in the regulation of cell proliferation and differentiation The expression of genes related to differentiation function is the most critical event in cell differentiation. These genes are in the repressed state in stem cells. Evidence has accumulated to indicate that DNA methylation plays a major role in the repression of certain genes (4–6). DNA methylation is taking place on the cytosine residues as 5mC, which occur exclusively in the CG sequence on the symmetric sites of DNA duplex. It takes two cell cycles of DNA hypomethylation for the removal of methylated sites and the expression of genes so affected (7–9).

DNA methylation is the most important biological methylation related to cell proliferation and differentiation, because of its apparent involvement in the regulation of gene expression. However, rRNA methylation also plays an important role in this respect. Most rRNA methylation is taking place on the 2'-o- ribose moieties. Such methylation is essential to protect rRNA sequences during biogenesis of ribosomes (10). rRNA's are synthesized first as a large 45 S precursor, which is processed in the nucleus to yield two ribosomal subunits. All of the methylated nucleosides are confined to the ribosomal RNA sequences. If these rRNA sequences do not have full compliment of methylated nucleosides, these sequences will also be degraded as those non-conserved sequences. Thus, the production of ribosomes depends greatly on the methylation of pre-rRNA.

Production of ribosomes is necessary to prepare the cells to enter S phase. It is essential that proteins needed for the replication of chromosomes are available prior to the engagement of DNA synthesis. If the production of ribosomes is selectively prohibited after growth stimulation by employing actinomycin D (11), which is a selective inhibitor of rRNA synthesis, or by shifting to the non-permissive temperature of a temperature sensitive mutant (12), DNA synthesis will also be aborted, and the cells terminate at G1 phase. These experiments clearly show that ribosome production is an absolute prerequisite to commit the cells to replication.

Role of abnormal methylation enzymes in malignant growth

With nucleic acid methylations demonstrated to play such important roles as the regulation of gene expression and ribosome production, a very important role must be ascribed to methylation enzymes. Methylation enzymes are a ternary enzyme complex consisting of MAT-MT-SAHH. There are a wide variety of MTs. Each individual MT is a very specific enzyme, and has its own unique function. But by virtue of association with the same pair of MAT and SAHH, MTs become a family of enzymes regulated by a common mechanism. Methylation enzymes are normally regulated by an activating effector such as steroid hormone in case of a steroid hormone target tissue (13). In the absence of such an activating effector, the ternary enzyme complex dissociates into individual enzymes which are quickly destroyed by endogenous proteolytic enzymes. It appears that the ternary enzyme complex is the stable and functional entity of methylation enzymes. Evidently normal methylation enzymes are totally dependent on an exogenous activating effector. In non-steroid hormone target tissues, activating effectors of methylation enzymes can be produced in response to growth stimulation.

Methylation enzymes of cancer cells are different from these of normal cells. The difference is due to toe association of methylation enzymes with a cancer specific protein factor. These abnormal methylation enzymes were discovered by Liau et al.(14–16) who presented evidence to show that cancer methylation isozymes displayed kinetic properties distinctly different from their normal counterparts. The Km values for the normal isozyme pairs which are designated with a sur-L, are 3 µM methionine and 0.35 µM adenosine for $MAT^L$ and $SAHH^L$, respectively. Those for the cancer isozymes, which are designated with a sur-LT, are 20 µM methionine and 2.2 µM adenosine for $MATL^T$ and $SAHH^{LT}$, respectively. The existence of an altered cancer MAT isozyme was confirmed by Surfrin and Lombarini (17) and by Kappler et al.(18). The cancer specific protein factor not only enhances enzyme activity and alters kinetic properties, but also changes the stability and regulation of ternary methylation enzymes. This factor acts like an activating effector of normal methylation enzymes to keep cancer methylation enzymes in extremely stable and active forms. Instead of relying on an exogenous activating effector, cancer cells generate an endogenous protein factor to ensure an efficient methylation system responsible for streamline production of functional RNAs needed for cell proliferation, and the reproduction of DNA methylation pattern to maintain malignant phenotype. Thus, abnormal methylation enzymes are clearly the most critical problem of cancer.

The altered cancer $MAT^{LT}$ was shown to be present in primary and transplantable rat hepatomas (15), and human cancers xenografted into athymic nude mice which included melanomas, sarcomas, a lymphoma, and adenocarcinomas of the colon, lung, breast, liver, ovary, uterus and nasopharynx (19). A surgical cancer tissue and HL-60 leukemia cells in culture also showed the same abnormality. Whereas enzyme levels of MAT$^{LT}$ were invariably elevated in cancer tissues, there existed a good correlation between levels of enzyme and growth rates of xenografted human cancers (19). Abnormal methylation enzymes were, however, never detected in normal tissues, including rapidly proliferating tissues such as regenerating liver, fetal tissues, bone marrow cells, and intestinal mucosa. Therefore, abnormal methylation enzymes are a specific abnormality associated with cancer. Since abnormal methylation enzymes play an important role in the promotion of malignant growth, they offer an opportunity for therapeutic intervention. The association with a cancer specific protein makes abnormal cancer methylation enzymes to respond differently to regulatory effectors in comparison with normal methylation enzymes. Our studies indicated that cancer RNA methylation enzymes responded markedly to inhibitory effectors such as oligonucleotides and intercalating agents, but only marginally to stimulatory effectors such as ATP and polyphosphate (10, 20). In stark contrast, normal RNA methylation enzymes responded markedly to stimulatory effectors, but not at all to inhibitory effectors. So obviously abnormal cancer methylation enzymes are the selective targets for cancer intervention.

Abnormal methylation enzymes as selective targets for differentiation therapy of cancer As above described, abnormal methylation enzymes are the roots of cancer problems, which effectively block cancer cells from entering differentiation pathways. It follows that the elimination of abnormal methylation enzymes should enable cancer cells to undergo terminal differentiation. As a matter of fact, our earlier experiments showed that this assumption was correct. The treatment of Novikoff ascites hepatoma resulted in the conversion of abnormal methylation enzymes into normal methylation enzymes (16), a delayed inhibition of macromolecular synthesis, and the termination of cell growth (21). The effect of poly (I)(C) most likely is an indirect effects since poly (I)(C) is unable to get inside the cell. It has been demonstrated that poly (I)(C) was capable of inducing oligoisoadenylate synthetase like interferon (22). The product of this induced enzyme, oligoisoadenylate which is a trinucleotide, may be the inhibitory effector responsible for the elimination of abnormal methylation enzymes. We have previously demonstrated that cancer rRNA methylation enzymes were sensitive to the inhibition by oligonucleotides, particularly trinucleotides (10). Oligonucleotides are the products of differentiated cells. Natural products which have similar function as oligonucleotides include conjugated oligopeptides and organic acids (23, 24). Such natural products possessing selective antitumor effect have been named antineoplastons by Burzynski (25). Antineoplastons are low molecular weight metabolites. In the kidney low molecular weight metabolites get back to the blood stream after glomerular filtration by reabsorption. Reabsorption is often incomplete. Thus s a normal person excretes a small amount of antineoplastons constantly. However S a healthy person is able to maintain a balance S so that there are always enough antineoplastons circulating to suppress malignant evolution. Liau et al. called such a natural chemical defense mechanism chemo-surveillance (26).

The active component of antineoplastons have been purified which showed pronounced activity in the induction of terminal differentiation of HL-60 cells (23) and in the inhibition of colony formation of HBL-100 cells (24). One active preparation contains primarily acidic peptides conjugated with pigment, and the other preparation contains primarily organic acids Both have similar biological activities e despite different chemical forms. When tested on partially purified MAT isozymes, these active preparations were shown to inhibit the abnormal cancer isozyme and convert it into the normal isozyme. It appears that the active components of antineoplastons selectively antagonize the cancer specific protein factor of MAT$^{LT}$, and eliminate the influence of this factor on the methylation enzymes. The antitumor mechanism is mediated through the modulation of abnormal methylation enzymes, resulting in hypomethylation of DNA and pre-rRNA (9). As a consequence, cancer cells are induced to undergo terminal differentiation. The effect is selective on cancer cells, since normal cells do not have that cancer specific protein factor for these active components to interact.

From enzymatic point of view, the conversion of abnormal methylation enzymes into normal methylation enzymes is the critical mechanism to trigger terminal differentiation. Analyses of intracellular pool sizes of AdoMet and AdoHcy strongly support the conclusion above reached. It has been shown by De La Rosa et al. (27) that the pool size of AdoMet of cancer cells was constitutively elevated. This finding is consistent with the higher Km of the cancer MAT isozyme. Studies conducted by Chiba et al. (28) indicated that when HL-60 cells became terminally differentiated, both pool sizes of AdoMet and AdoHcy shrunk, reflecting precisely the conversion of higher Km abnormal cancer methylation enzymes into lower Km normal enzymes. It appears that studies from different point of views have come to the same conclusion that abnormal methylation enzymes are responsible for denying cancer cells to undergo terminal differentiation.

Natural chemo-surveillance and the evolution of cancer

If human bodies are equipped with antineoplastons to suppress the evolution of cancer, why people get cancer? It is the same question as asking why people get sick when immune-surveillance is operating? Obviously surveillance mechanisms break down, so people get sick. Our studies indicated that cancer patients were deprived of chemo-surveillance because of excessive excretion of low molecular weight metabolites (26, 29). Excessive excretion results in the depletion of endogenous antineoplastons, thus creating conditions favorable for the multiplication of cancer cells. In addition, the growth of cancer cells causes even greater loss of endogenous antineoplastons. Eventually chemo-surveillance is totally non-functional in terminal stage cancer patients. Although abnormal methylation enzymes are the most important cause of cancer problems, the destruction of chemo-surveillance is another important factor which has a pivotal influence on the pathogenesis of cancer. If a therapy can deal with both contributing factors of cancer, namely can eliminate abnormal methylation enzymes and restore chemo-surveillance, the therapy will have a greater chance to succeed.

Antineoplaston preparations purified from urine appears to take care of both contributing factors of cancer very well. On one hand abnormal methylation enzymes were corrected to become normal enzymes, and on the other hand the excessive urinary excretion of peptides was quickly reversed (23, 29). The efficacy of antineoplaston therapy was indeed remarkable (30).

The reason why cancer patients excrete large amounts of low molecular weight metabolites is probably attributable to inflammation. Inflammation causes macrophages to release cachectin, and cachectin is responsible for the symptom known as cachexia which is characterized by excessive excretion of metabolites, increased catabolism including lipid movilization, and anorexia (31–33). Acute inflammation lasts only a short while. Therefore it does not have much effect on the evolution of cancer. Chronic inflammation because of long lasting effect is definitely a contributing factor on cancer. For example, quite a number of patients suffering from AIDS or hepatitis B become cancer patients. Cancer cells are themselves sources of chronic inflammation because of expression of genes not normally expressed in wealthy cells. The more the growth of cancer cells, the worse the cachexia becomes. An effective means to control cachexia will be beneficial in cancer therapy. Cachexia, however, is totally neglected by conventional cancer therapists. We have previously shown that cytotoxic drugs induced excessive excretion of peptides (26). Thus, cytotoxic drugs contribute to the destruction of chemosurveillance. The body eventually become defenseless after long term application of cytotoxic drugs. If there are surviving cancer cells not responding to cytotoxic therapy, these cells are going to multiply very well. The therapeutic efficacy of cytotoxic drugs depends on the total elimination of cancer cells, a task not easily attainable. In contrast, antineoplaston therapy quickly restores chemo-surveillance, and this natural defense mechanism is capable of taking care of the residual cancer cells. There is no need to wipe out a whole population of cancer cells.

Phenylacetyl glutamine, a component of antineoplaston preparations, is capable of reversing excessive excretion of peptides normally associated with cancer patients. This compound is inactive by itself on the growth of malignant cells in culture. Nevertheless, it is producing encouraging results on the therapy of early stage cancers (26), and on the prevention of chemical carcinogenesis (34–36). Its therapeutic and chemopreventive effect are likely attributable to its ability to restore and to protect chemo-surveillance. It has been demonstrated that induction of cancer was much easier to take place in cultured cells than in intact animals (37, 38). This is because chemo-surveillance is operating in intact animals, and it takes time for this chemical protection mechanism to break down in order for the symptom to show up. Inflammatory agents such as proton oil serve as promoters to enhance carcinogenesis, and agents such as phenylacetyl glutamine which have the ability to keep chemosurveillance intact can serve as chemopreventive agents. In summary, chemo-surveillance if utilize properly can be very useful to assist cancer therapy or prevention.

Role of helper inducers in differentiation therapy

Inducers of differentiation can directly or indirectly convert abnormal methylation enzymes into normal enzymes. Antineoplastons are direct inducers, and retinoic acid, interferon and poly(I)(c) (polyinosinic acid:cytidylic acid) are indirect inducers (9, 16, 39). The effectiveness of indirect inducers relies totally on the availability of receptors. Because of this limitation, responding cancers are only limited to a few. Recently Liau et al. reported a group of chemicals, although devoid of differentiation inducing activity, could nevertheless greatly potentiate the activity of inducers (40). Chemicals as such were accordingly named helper inducers. Helper inducers are mostly inhibitors of component enzymes of ternary methylation enzymes, such as competitive inhibitors of MAT herein described. Butyric acid is the most effective helper inducer among competitive inhibitors of MAT, but phenylacetic acid is also active (40). Helper inducers of this group are relatively nontoxic (41–43). From therapeutical point of view, helper inducers are valuable because they can greatly increase the scope of responding cancers, particularly toward indirect inducers. From economical point of view, helper inducers are also valuable because they can greatly reduce the burden of patients. These chemicals are cheap and abundant. In some special cases, helper inducers can be used alone to achieve cancer therapy. Brain is a special compartment shielded by a blood-brain barrier. Exogenous chemicals are not easy to get in, and endogenous products are also not easy to get out. The loss of endogenous antineoplastons in brain compartment is not as great as that of other compartments. Therefore, the employment of helper inducers alone can achieve effective therapy of brain cancers, particularly astrocytoma. Astrocytoma is not responding to any cytotoxic drugs. Thus so far, phenylacetic acid is the only drug astrocytoma responds well. By the same token, helper inducers can be used for the treatment of cancer at early stage, and for the prevention of cancer.

SUMMARY OF THE INVENTION

We recognize the important contribution of helper inducers in the differentiation therapy and the chemoprevention of cancer, a systemic study was conducted to explore helper inducers. We screened effective helper inducers on one hand, and on the other hand, modified chemical forms to improve their effectiveness and applicability. We have come to the conclusion that the following chemicals are excellent helper inducers: methyl and ethyl phenylacetamides, ethyl phenylacetate, 2,4-dichlorophenylacetic acid, and indole acetic acid. Methyl and ethyl phenylacetamides, ethyl phenylacetate, 2,4-dichlorophenylacetic acid, and indole acetic acid are competitive inhibitors of MAT.

The present invention provide a pharmaceutical composition for differentiation therapy and prevention of cancer, preferably brain and prostatic cancer, comprises one or more than one compounds as help inducers selected from the group consisting of methyl phenylacetamide, ethyl phenylacetamide, ethyl phenylacetate, 2,4-dichlorophenyl acetic acid, and indole acetic acid.

Preferably, the pharmaceutical composition has a form suitable to be administered orally, parenterally, or topically.

Preferably, the pharmaceutical composition further comprises an active compound as an differentiation inducer for differentiation therapy of cancer.

DETAILED DESCRIPTION OF THE INVENTION

Figure 1:
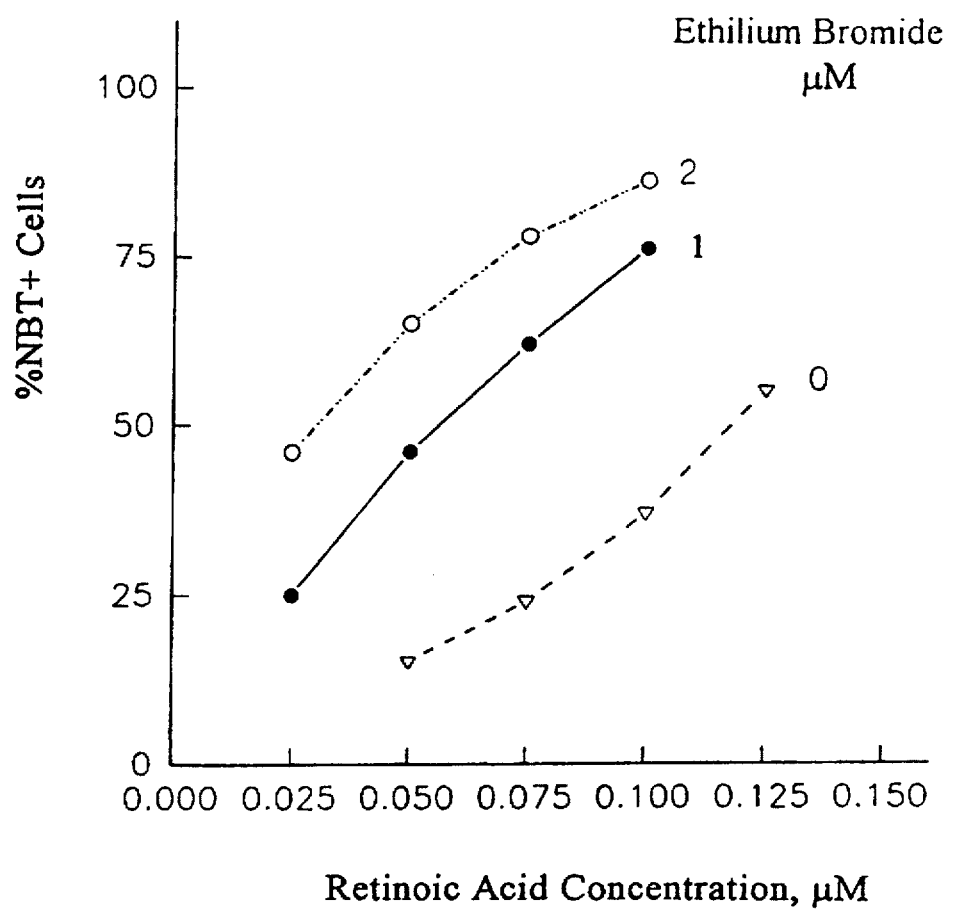
FIG. 1 is a plot which shows potentiation of RA-induced terminal differentiation by ethidium bromide, wherein the concentrations of ethidium bromide used are 0.0 μM (▽), 1.0 μM (●) and 2.0 μM (○), respectively.

Although named as helper inducers, their application in the differentiation therapy of cancer is beyond helping role to potentiate the therapeutic efficacy of differentiation inducers. Helper inducers are actually essential components to achieve differentiation therapy. We have noticed that differentiation induced in the presence of helper inducers could reach greater extent of completion as compared to inducers alone (40). With inducers alone, NBT+ cells rarely exceeded 85%. There was always a small fraction of uninduced cells. This small fraction of uninduced cells is the reason why the remission resulting from RA therapy is so short (44). Differentiation is a long process which must go through two cell cycles of uninterrupted DNA hypomethylation (45–47). If cells are damaged during this process, DNA synthesis can not progress to completion. These damaged cells if repaired are likely to revert back to the original malignant state. And the symptom reappears. Malignant cells have elevated levels of methylation enzymes. These enzymes are dependent upon cancer specific protein factor to maintain stability as ternary enzyme complexes. Once that cancer specific protein factor is antagonized by antineoplastons or antineoplaston-like factors induced by differentiation inducers, ternary methylation complexes will dissociate to give rise to individual component enzymes. Some of methyltransferases in monomeric forms may become nucleases, better known as latent nucleases, to cause cell damage (10), resulting in the disruption of differentiation. The employment of helper inducers is designed to control the damage attributable to latent nucleases so that differentiation can reach completion. It is clear that helper inducers are also indispensable components of differentiation therapy. Helper inducers can facilitate differentiation and reduce the chance of recurrence.

I. Preparation of derivatives of phenylacetic acid

The establishment of phenylacetic acid as helper inducer (40) and the effectiveness of phenylacetic acid in the treatment of astrocytoma (30, 43) have been well documented. It is, however, not a good helper inducer. It requires a few mM quantities to show biological activity as helper inducer. Besides, the odor is offensive. There are rooms for improvement. We have discovered that following derivatives of phenylacetic acid were much better on the basis of activity and the odor they generated.

I-1. Preparation of N-substituted phenylacetamides

N-substituted phenylacetamides are all known compounds listed in reference 51. However, we have designed a procedure shown in scheme 1 to prepare these derivatives.

Scheme 1

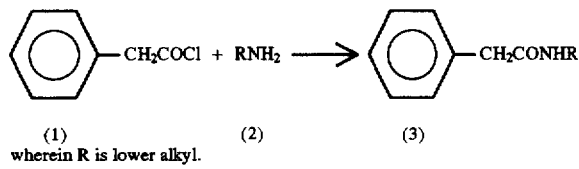

(1)   (2)   (3)

wherein R is lower alkyl.

Phenylacetyl chloride was reacted with methylamine or ethylamine in benzene. The products were purified by column chromatography and recrystallization.

EXAMPLE I-1-1.

phenylacetamide (3-1)

Dissolved 15 g (0.1 mol) of phenylacetyl chloride in 100 ml of benzene. While stirring on a magnetic stirrer, introduced ammonia gas into the benzene solution at 20°–30° C. After reaction, the solid was collected by filtration, washed with water, and dried. The filtrate was washed in a separators funnel with water, and dehydrated with anhydrous magnesium sulfate. The solution was evaporated to dryness in a rotary evaporator. The residue together with the solid above obtained was purified by column chromatography employing silica gel-chloroform system, and recrystallization with chloroform to yield white crystal as compound 3-1. Yield, 11 g (80%).

mp.: 153°–155° C.; IR(KBr)$v_{max}$: 3300, 3120(NH), 1670 (C=O)cm$^{-1}$; [1] H-NMR (CDCl$_3$)3.58(s,2H,—CH$_2$), 5.60(br, 2H,—NH$^2$), 7.24–7.30(m, 5H,—C$_6$H$_5$), MS, m/z: 135(M$^+$); element analysis: C$_8$H$_9$NO, calculated value: C:71.09, H:6.71, N: 10.36, found value: C: 17.15, H: 6.93, N: 10.26

EXAMPLE I-1-2

N-Methyl phenylacetamide (3-2)

Dissolved 15 g(0.1 mol) of phenylacetyl chloride in 100 ml of benzene. While stirring on a magnetic stirrer, introduced methylamine into the benzene solution at 20°–30° C. Followed the procedure of compound 3-1 for the purification of the product to yield N-methyl phenylacetamide as light yellowish crystal. Yield, 12 g (80%).

mp.: 56°–59° C.; IR(KBr)$v_{max}$: 3340(NH), 1630(C=O) cm$^{-1}$; $^1$H-NMR(CDCl$_3$)δ:2.75(s,3H,—CH$_3$), 3.59(s,2H,—CH$_2$), 5.59(br,1H,—NH ), 7.28–7.31(m,5H,—C$_6$H$_5$); MS, m/z: 149(M$^+$); element analysis: C$_9$H$_{11}$NO, calculated value: C:70.04, H: 8.08, N: 10.21, found value: C: 70.18, H: 8.05, N: 10.07

EXAMPLE I-1-3:

N-Ethyl phenylacetamide (3-3)

Dissolved 15 g (0.1 mol) of phenylacetyl chloride in 100 ml of benzene. While stirring on a magnetic stirrer, added 25 g of ethylamine (0.5 mol) into the benzene solution at 20°–30° C. After reaction, the solution was washed with water, dehydrated with anhydrous magnesium sulfate. The solvent was removed by rotary evaporator and the residue was purified by column chromatography as compound 3-1 to yield N-ethyl phenylacetamide as yellowish crystal. Yield, 14 g (85%).

mp.: 72°14 74° C.; IR(KBr)$v_{max}$: 3360(NH), 1630(C=O) cm$^{-1}$; $^1$H-NMR(CDCl$_3$)δ: 1.02(t,3H,—CH$_3$), 3.25(m,2H,—N—CH$_2$), 3.50(s,2H,—CH$_2$—CO—), 7.20–7.33(m,5H,—C$_6$H$_5$); MS. m/z: 163(M$^+$); element analysis: C$_{10}$H$_{13}$NO, calculated value: C:73.59, H: 8.03, N: 8.58, found value: C: 73.67, H: 8.00, N: 8.41

I-2. Preparation of alkyl phenylacetates:

Esters of phenylacetic acid are listed in references 52 and 53. We prepared these derivatives according to the standard procedure shown in scheme 2.

Scheme 2

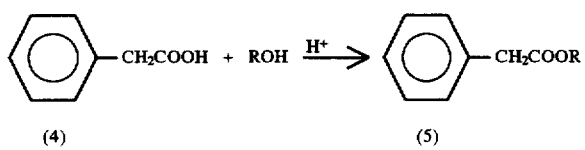

(4)   (5)

wherein R is lower alkyl.

In the presence of Lewis acid, phenylacetic acid was allowed to react with alcohol to yield respective ester.

EXAMPLE I-2-1

Methyl phenylacetate (5-1)

Dissolved 13 g (0.1 mol) of phenylacetic acid in 500 ml of anhydrous methanol. Introduced HCl gas, while refluxing for 3 hours. The solvent was then removed by evaporation. Dissolved the ester in benzene, which was successively washed with water and 10% NaOH. The organic layer was dehydrated with anhydrous magnesium sulfate. The solvent was again removed by evaporation. Methyl phenylacetate was finally purified by column chromatography employing silica gel chloroform system. The solvent was removed by evaporation to yield yellowish liquid. Yield, 6 g (40% ).

bp.: 218° C.; IR(KBr)$v_{max}$: 1700(C=O)cm$^{-1}$; $^1$H-NMR (CDCl$_3$)δ: 3.62(s,2H,—CH$_2$), 3.70(s,3H,—CH$_3$), 7.30–7.32 (m,5H,—C$_6$H$_5$); MS, m/z: 150(M$^+$)

EXAMPLE I-2-2

Ethyl phenylacetate (5-2)

Dissolved 13 g (0.1 mol) of phenylacetic acid in 500 ml of anhydrous ethanol. The reaction and purification of the product were as those described for methyl phenylacetate. Ethyl phenylacetate was a yellowish liquid. Yield, 6.5 g (40% ).

bp.: 227° C.; IR(KBr)$v_{max}$: 1700(C=O)cm$^{-1}$; $^1$H-NMR (CDCl$_3$)δ: 1.24(s,3H,—CH$_3$),3.61(s,2H,—CH$_2$—CO—), 4.15(s,2H,—OCH$_2$), 7.29–7.32(m,5H,—C$_6$H$_5$); MS, m/z: 164(M$^+$)

I-3. Other helper inducers we have so for discovered such as 2,4-dichlorophenyl acetic acid, and indole-3-acetic acid were obtained from Sigma Chemical Company.

Experimental materials herein described such as all trans-retinoic acid, phenylacetic acid, phenylacetyl chloride, butyric acid, and hexanoic acid were obtained from E. Merck Darmstadt.

II. Determination of the activity of helper inducers

The procedure developed by Liau et al. (40) was employed for the determination of the activity of helper inducers. The procedure was based on the NBT assay of the induced differentiation of HL-60 cells. HL-60 cells were subcultured at an initial concentration of 1.5×10$^5$ cells/ml. Each flask contained 10 ml. Flasks were divided into several sets of 5 flasks containing RA from 0 to 0.125 μM. RA was dissolved in methanol. The volume of methanol added was limited to 2% so that the growth and differentiation of HL-60 cells were not appreciably affected. One set served as control, while helper inducers of the indicated amounts were added to other sets. After 96 hours cell number was counted, and NBT assay was conducted as previously described (40). NBT+ cells of the control without any addition were always below 4%. In the presence of helper inducers alone, the control numbers were in general below 10%. The respective control value was subtracted from each experimental value. ED$_{50}$ values which are defined as effective dosages to cause induction of 50% NBT+ cells, can be obtained from plots of NBT+values versus concentrations of RA in the absence and presence of helper inducers. As shown in FIG. 1 ED$_{50}$ of RA is 0.12 μM. In the presence of 1 μM or 2 μM ethidium bromide as helper inducer, this value is reduced to 0.056 μM or 0.03 μM, respectively. The reductive index is defined as ED$_{50}$ in the presence of helper inducer divided by ED$_{50}$ in the absence of helper inducer. This value bears an inverse relationship with the effectiveness of the helper inducer.

Figure 2:
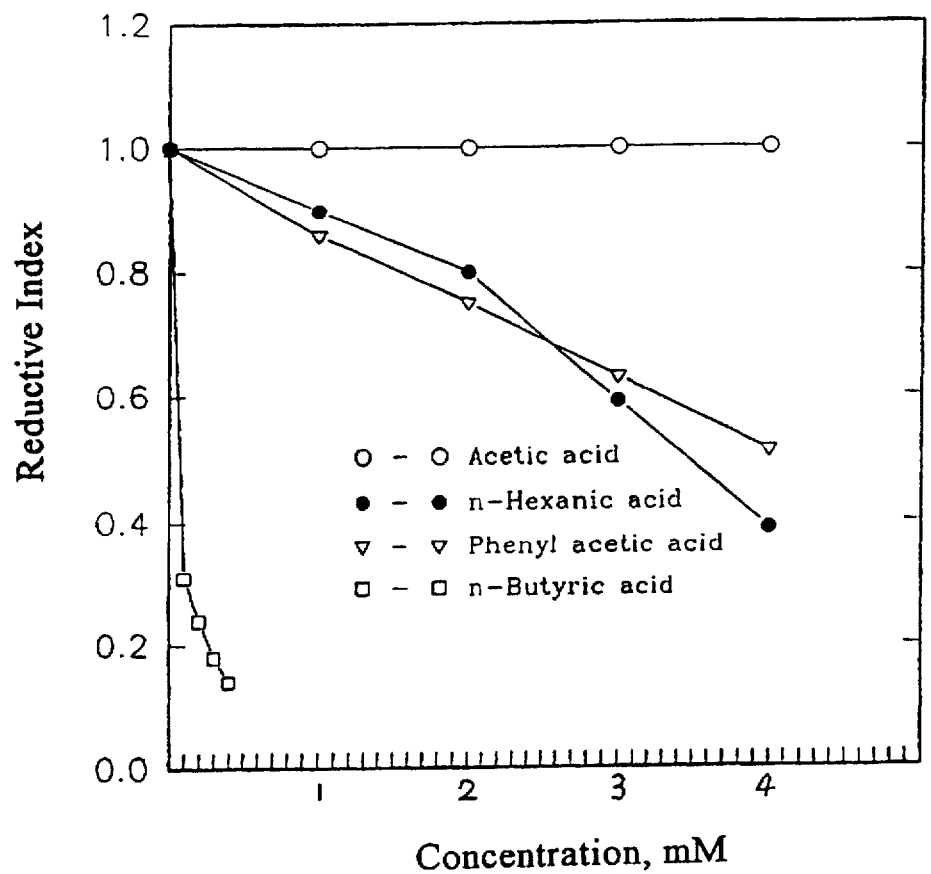
FIG. 2 is a plot which shows effectiveness of acetic acid (○), butyric acid (□), hexanoic acid (●), and phenylacetic acid (▽) as helper inducers.

The biological activity of helper inducers is greatly influenced by the chemical structure. As shown in FIG. 2, butyric is the most active helper inducer among competitive inhibitors of MAT. Acetic acid is completely ineffective. The addition of a phenyl group to acetic acid restores some activity. Hexanoic acid is much less active compared to butyric acid. Although butyric acid is a very active helper inducer, it is not a suitable therapeutic drug because it is quickly metabolized. In addition, the odor is very offensive. Phenylacetic acid is a stable chemical metabolically, but the activity is not that good. The odor of phenylacetic acid is offensive too. Through a systemic search, we have discovered the following compounds to serve as excellent helper inducers.

II-1. N-Methyl phenylacetamide

Figure 3:
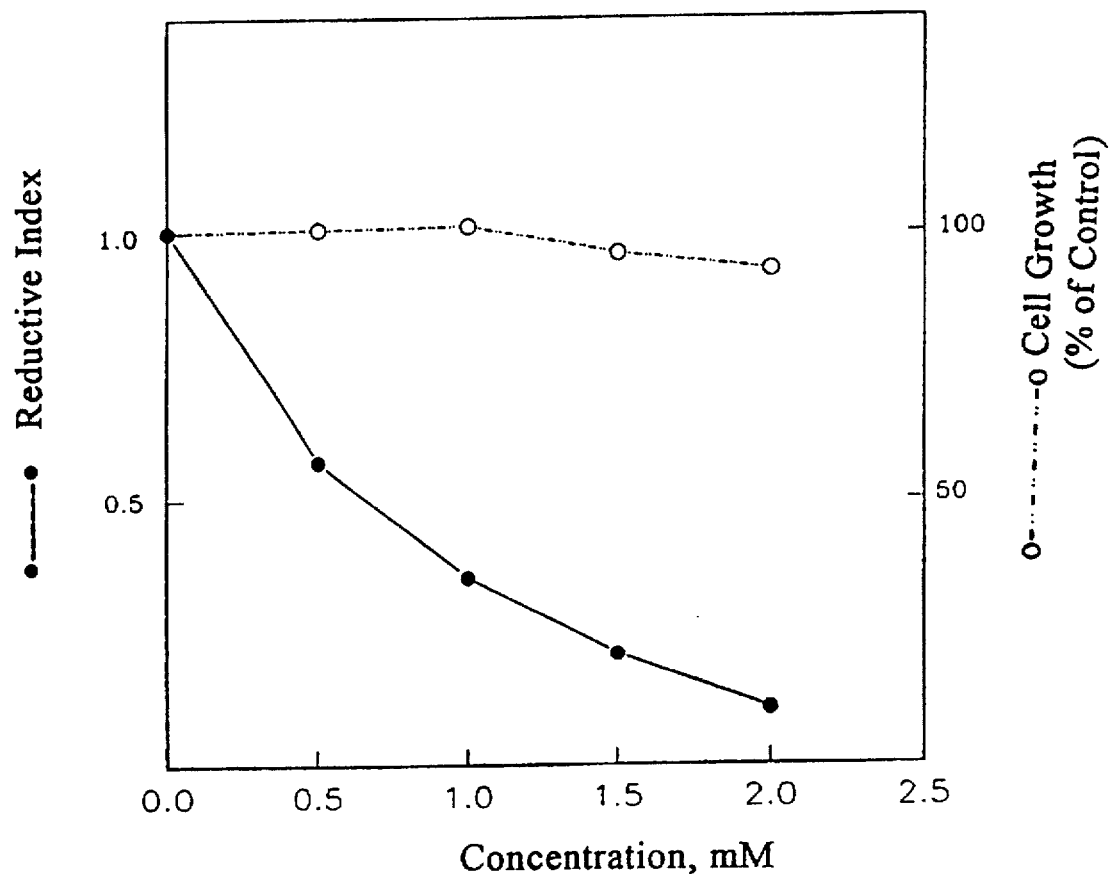
FIG. 3 is a plot which shows helper inducer activity of and cell inhibitory effect by methyl phenylacetamide.

N-Methyl phenylacetamide was dissolved in methanol for the determination of its activity as helper inducer. As shown in FIG. 3, it takes 0.65 mM to reach a reductive index of 0.5. The corresponding concentration of phenylacetic acid is 4 mM. Therefore, it is a good improvement. The growt of HL-60 was not affected by this compound below 2 mM. It does not have offensive odor. It is a great improvement in this respect too. The only disadvantage is that it is not soluble in water. It can not be formulated as a parenteral preparation. It is perfectly all right to be formulated as oral preparations.

II-2. Ethyl phenylacetamide

Figure 4:
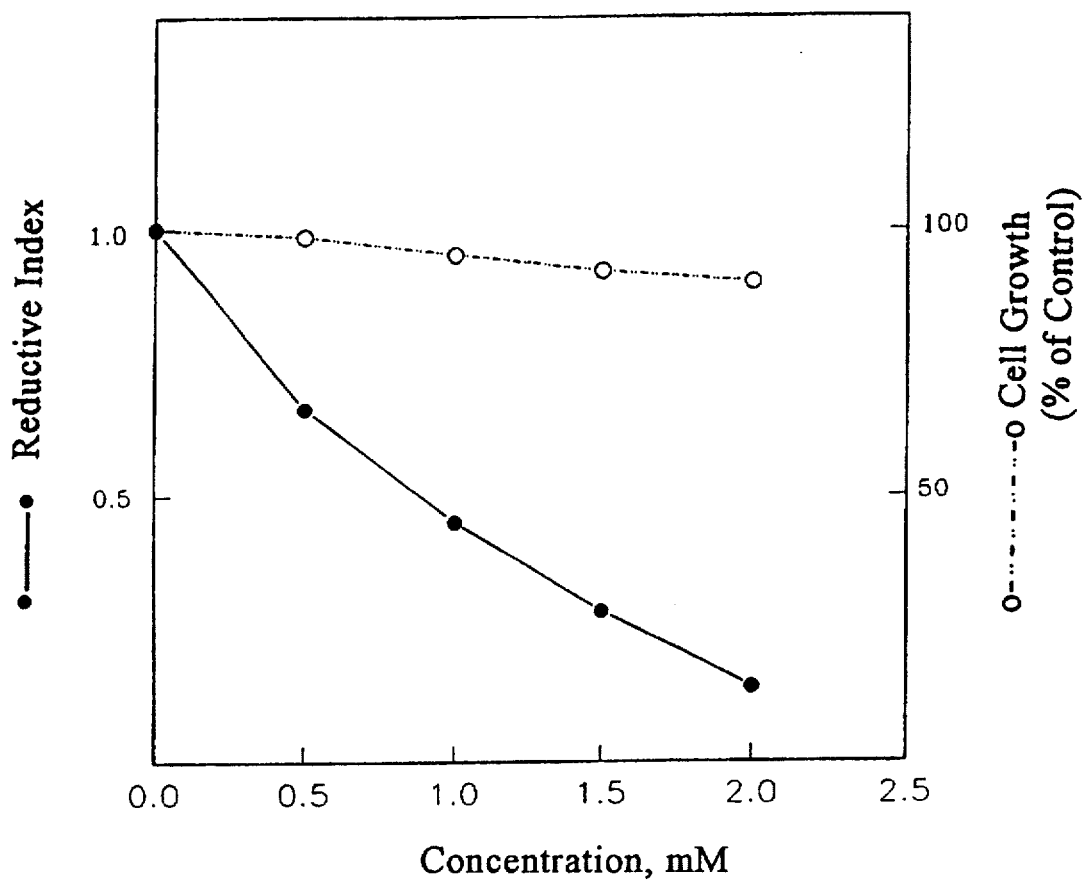
FIG. 4 is a plot which shows helper inducer activity of and cell inhibitory effect by ethyl phenylacetamide.

Ethyl phenylacetamide is very much alike methyl phenylacetamide with respect to chemical properties and biological activity. It is slightly less active, requiring 0.87 mM to reach a reductive index of 0.5 as shown in FIG. 4.

II-3. Ethyl phenylacetate

Figure 5:
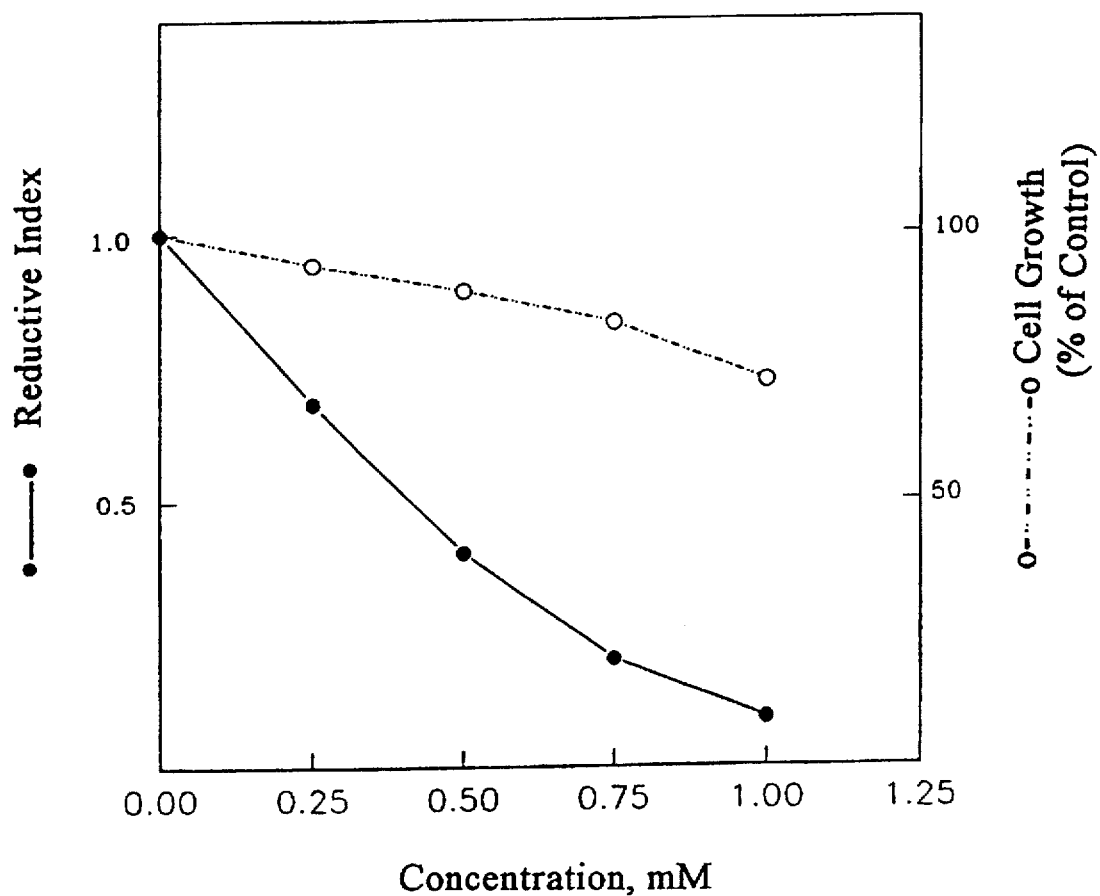
FIG. 5 is a plot which shows helper inducer activity of and cell inhibitory effect by ethyl phenylacetate.

This is a yellowish liquid with pleasant smell. It was dissolved in methanol for the determination of its activity as helper inducer. As shown in FIG. 5, it is a very active helper inducer. The activity is 10-fold greater than phenylacetic acid, requiring 0.4 mM to reach a reductive index of 0.5. It is very easily hydrolyzed in contact with acid. Therefore, the soft gel preparation must have an enteric coating to avoid acid hydrolysis.

II-4. 2,4-Dichlorophenylacetic acid

Figure 6:
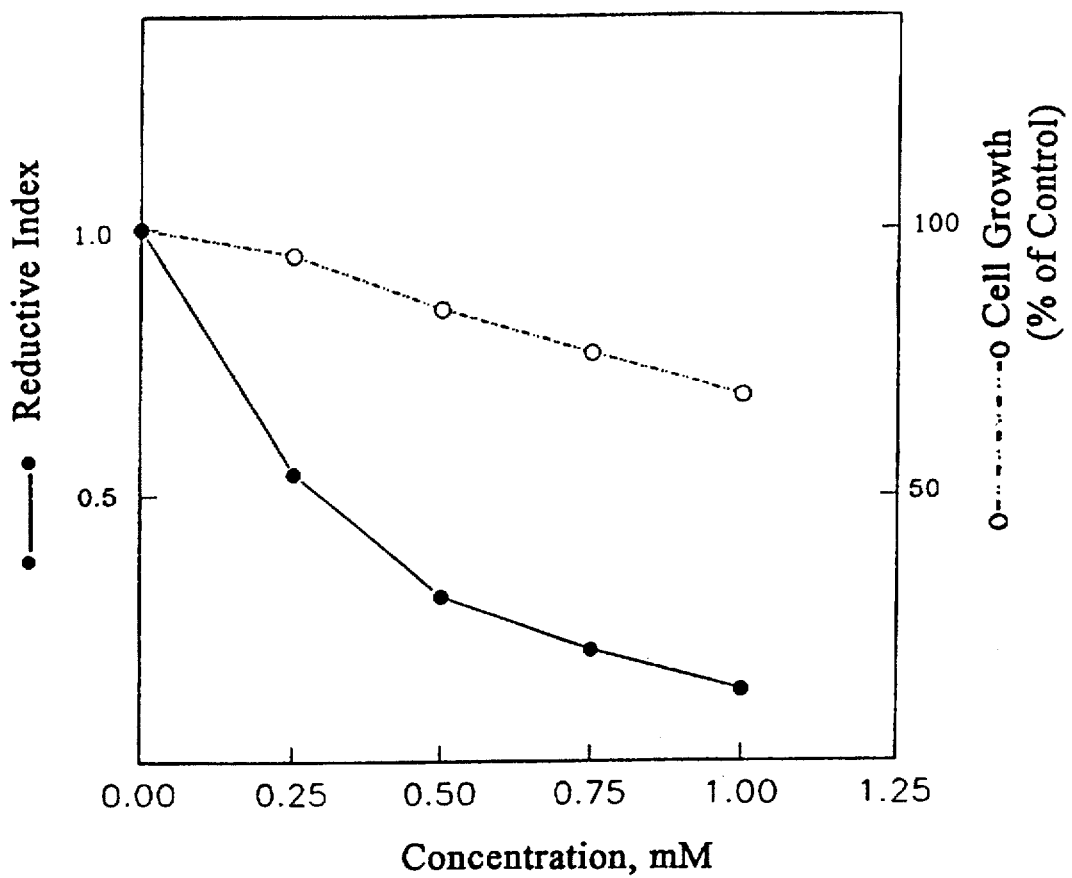
FIG. 6 is a plot which shows helper inducer activity of and cell inhibitory effect by 2,4-dichlorophenyl acetic acid.

This is a colorless crystal with pleasant smell. It was dissolved as sodium salt for the determination of its activity as helper inducer. As shown in FIG. 6 it is also a very active helper inducer, requiring 0.3 mM to reach a reductive index of 0.5. Because of a chlorine-substituted derivative, its toxicity must be checked in order to consider it for clinical application. It certainly can be considered for short-term application of terminal cancer patients.

II-5. Indole acetic acid

Figure 7:
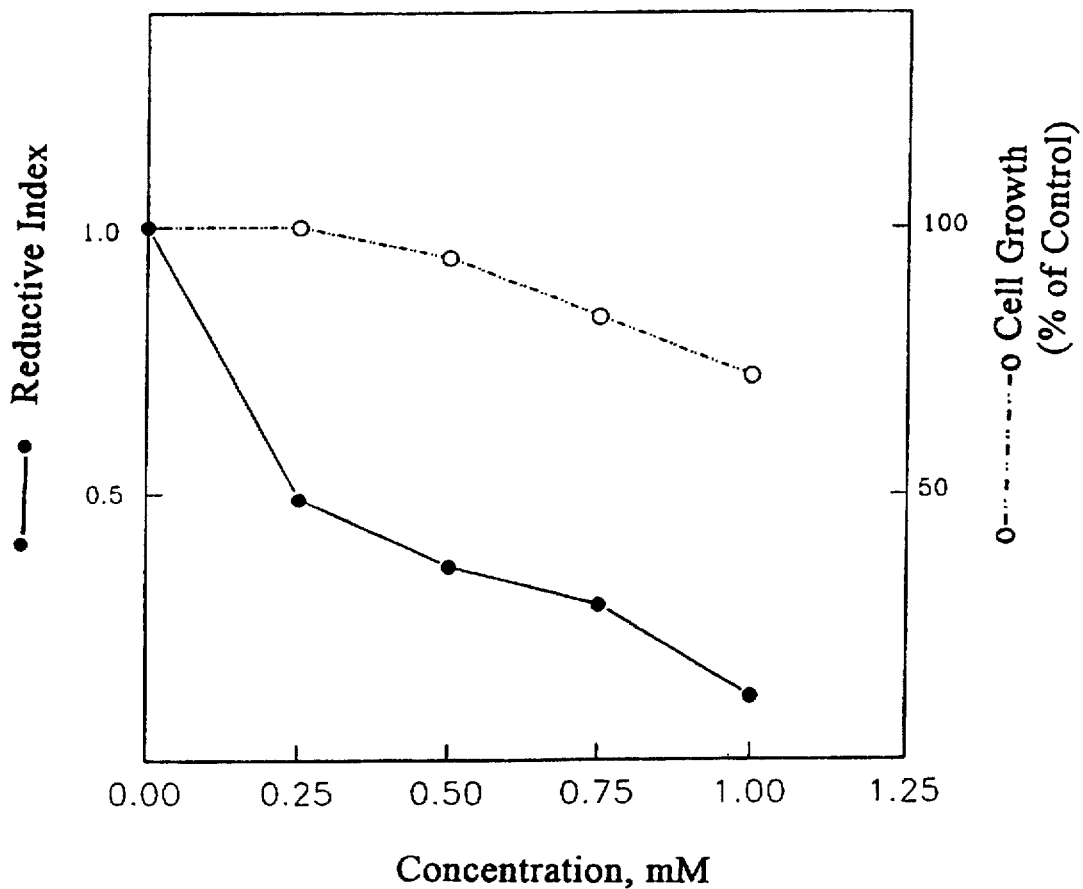
FIG. 7 is a plot which shows helper inducer activity of and cell inhibitory effect by indole acetic acid.
Figure 8:
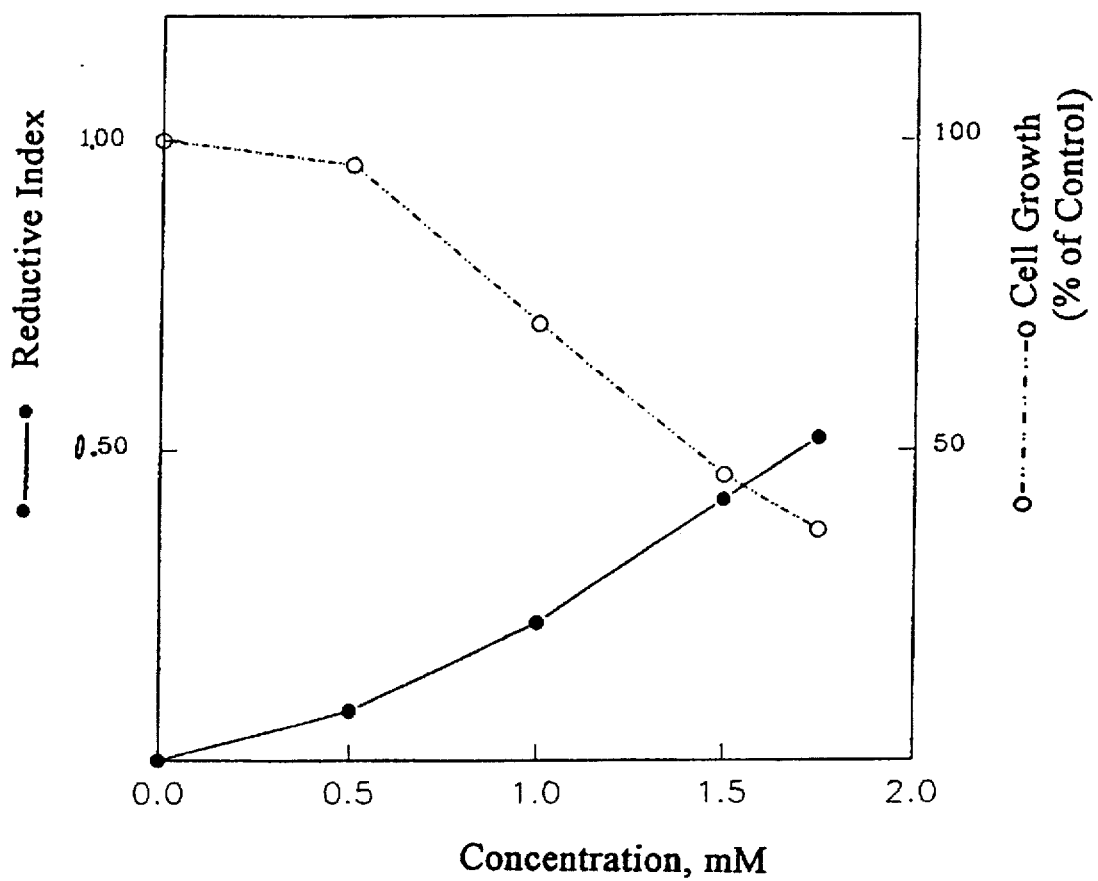
FIG. 8 is a plot which shows indole acetic acid as inducer of terminal differentiation.

Replacement of phenol group with indole group greatly increases the activity as shown in FIG. 7, it takes 0.25 mM to reach a reductive index of 0.5. A very active help inducer often by itself is also a formidable inducer. It is not surprising that indole acetic acid is active as inducer at concentration above 0.5 mM as shown in FIG. 8.

References:
(1). Quesada, J. R., Reuben, J., Manning, J. T., Hersch, E. M., and Gutterman, J. Alpha interferons for indution of remission in hairy call leukemia. N. Engl. J. Med., 310. 15–20, 1984.
(2). Huang, M. E.,Ye, Y. C.,Chen, S. R., Chai, J. R., Lu, J. X.,Zhoa, L.,Gu, L. J., and Wang, Z. Y., Use of all-trans retinoic acid in the treatment of acute promyelocytic leukemia. Blood, 72: 567–572,1988.
(3). Warrel, R. P. Jr., Frankel, S. R., Miller, W. H. Jr., Sheinberg, D. A., Itri, L.
M., Hellelman, W. N., Vyas,S., Andreeff M., Tafuri, A., Jakubowski, A., Gabrilove, J., Gordon, M. S. and Dmitrovsky, E. Differentiation therapy of acute promyelocytic leukemia with tretinoin(all-trans-retinoic acid). N. Engl.
J. Med., 324: 1385–1393, 1991.
(4). Doerfler, W., DNA methylation and gene activity. Annu. Rev. Biochem.,52: 93–124,1983.

(5). Jones P. A., Altering gene expression with 5-azacytidine. Cell, 40:484–486,1985.

(6). Cedar,H. DNA methylation and gene activity. Cell, 53:3–4,1988.

(7). Christman,J. K., Price, P.,Pechman, L., Randall,R. J., Correlation between hypomethylation of DNA and expression of globin genes in Friend erythroleukemia cells. Biochem 31: 53–61,1977.

(8). Jones, P. A., Taylor, S. M., Cellular differentiation, cytidine analogs and DNA methylation. Cell 20: 85–93, 1980.

(9). Liau, M. C., and Burzynski, S. R., Hypomethylation of nucleic acids: a key to the indution of terminal differentiation. Intl. J. Exptl. Clin. Chemother., 2:187–199, 1989.

(10). Liau, M. C., Hunt, M. E.., and Hurlbert, R. B., Role of ribosomal RNA methylases in the regulation of ribosome production in mammalian cells. Biochem. 15: 3158–3164, 1976.

(11). Epifanova, O. I., Abuladze, M. K., and Zoniovska, A. I., Effect of low concentrations of actinomycin D on the initiation of DNA synthesis in rapidly proliferating and stimulated cell cultures. Exp. Cell Res.,92:25–30.1975.

(12) Toniola, D., Weiss, H. K., and Basilio, C. A., Temperature sensitive mutation affecting 28S ribosomal RNA production in mammalian cells. Proc. Acad. Sci. USA, 70: 1273–1277, 1973.

(13). Liau, M. C., Chang, C. F., Saunders, G. P., and Tsai, Y. H., S-adenosylmethionine hydrolases as the primary target enzymes in androgen reculation of methylation complexes. Arch. Biochem. Biophys., 208:261–272,1981.

(14). Liau, M. C., Lin, G. W., and Hurlbert, R. B., Partial purification and characterization of tumor and liver S-adenosylmethionine synthetases. Cancer Res., 37:427-435, 1977a.

(15). Liau, M. C., Chang, C. F., and Becker, F. F., Alteration of S-adenosylmethionine synthetases during chemical hepatocarcinogenesis and in resulting carcinomas. Cancer Res., 39: 2113–2119, 1979.

(16). Liau, M. C., and Burzynski, S. R., Altered methylation complex isozymes as selective targets for cancer chemotherapy. Drugs Exptl. Clin. Res., 12(Suppl.1): 61–70, 1986.

(17). Sufrin, J. R., and Lombardini, J. B., Differences in the active site region of tumor versus normal isozymes of mammalian ATP: L-methionine S-adenosyltransferase. Mol. Pharmacol., 22: 752-759, 1982.

(18). Kappler, F., Hai, T. T., and Hampton, A., Isozyme-spectific enzyme inhibtor, 10 adenosine 5 -triphosphate derivatives as substrates or inhibtors of methionine adenosyltransferases of rat normal and hepatoma tissues. J. Med. Chem.,29: 318–322,1986.

(19). Liau, M. C., Chang, C. F.,and Giovanella, B. D., Demonstration of an altered S-adenosylmethionine synthetase in human malignant tumors xenografted into athymic nude mice. J. Natl. Cancer Inst., 64: 1071–1075, 1980.

(20). Liau, M. C., Lin, G. W., Knight, C. A., and Hurlbert, R. B., Inhibition of RNA methylation by intercalating agents. Cancer Res., 37: 4202–4210, 1977b.

(21). Liau, M. C., Smith, D. W., and Iluribert, R. B., Preferential inhibition of homopolyribonucleotides of the methylation of ribosomal ribonucleic acid and disruption of the production of ribosomes in rat tumor. Cancer Res., 35:2340–2349, 1975b.

(22). Chapekar, M. S., and Glazer, R. L, Effects of fibroblast and recombinant leukocyte interferons and double stranded RNA on ppp(2'–5')A synthesis and cell proliferation in human colon carcinoma cells in vitro. Cancer Res., 43 :2683,1983.

(23). Liau, M. C., Lee, S. S., and Burzynski, S. R., Differentiation inducing components of antineoplaston A5. Adv. Exptl. Alin. Chemother., 6/88:9–25,1988.

(24). Liau, M. C., and Burzynski, S. R., Separation of active anticancer components of antineoplaston A2, A3 and A5. Intl. J. Tiss. React., 12(Suppl.): 1–18, 1990a.

(25). Burzynski, S. R., Antineoplastons:Biochemical defense against cancer. Physiol. Chem.Phys.,8:275–279, 1976.

(26). Liau, M. C., Szopa, M., Burzynski, B., and Burzynski S. R., Chemosurveillance: A novel concept of the natural defense mechanism against cancer. Drugs Exptl. Clin. Res., 12(Suppl. 1): 71–76, 1987b.

(27). De La Rosa, J.,Geller, A. M., Legros, H. L., and Kotb,M., Induction of interleukin 2 production but not methionine adenosyltransferase activity or S- adenosylmethionine turnover in Jukat T-cell. Cancer Res.,52: 3361–3363,1992.

(28). Chiba,P.,Wallner, L., and Kaiser, E., S-Adneosylmethionine metabolism in HL-60 cells: effects of cell cycle and differentiation. Biochem. Biophys. Acta, 971:38–45,1988.

(29). Liau, M. C., Szopa, M., Burzynski, B., Burzynski, S. R., Quantitative assay of plasma and urinary peptides as an aid for the evaluation of cancer patients undergoing antineoplaston therapy. Drugs Exptl. Clin Res. 12(Suppl. I):61–70, 1987a.

(30). Burzynski, S. R., and Kubove, E., Initial clinical study with antiplaston A2 injections in cancer patients with five years follow-up. Drugs Exptl. Clin. Res., 13(Suppl. 1): 1–11,1987a.

(31). Clark, P. M. S., Kricka, L. J., and Whitehead, T. P.,Pattern of urinary proteins and peptides with rheumatoid arthritis investigated with the iso-dalt technique. Clin. Chem.,26:201,1980.

(32). Borek, E., et al. Altered excretion of modified nucleosides and βaminoisobutyric acid in subjects with acquired immunodeficiency syndrome or at risk for acquired immunodeficiency syndrome. Cancer Res.,46:2557,1986.

(33). Bar-Or, D.,Greisman, S. L., Kastendieck, J. G., Detection of appendicitis by measurement of uroerythrin. U.S. Pat. No. 5,053,389,1991.

(34). Kampalath, B. N., Liau, M. C.,Burzynski,B.and Burzynski, S. R. M., Chemoprevention by antineopalstons A10 of benzo (a) pyrene-induced pulmonary neoplasia. Drugs Exptl.Clin. Res.,13(Suppl.):51–56,1987.

(35). Kampalath, B. N., Liau, M. C.,Burzynski,B.and Burzynski, S. R., Protective effect of antineoplaston A10 in hepatocarcinogenensis induced by aflatoxin B1. Intl. J. Tiss. React., 12 (Suppl.):43–50,1990.

(36). Muldoon, T. G., Copland, J. A. and Hendry, L. B., Antineoplaston A10 activity on carcinogen-induced rat mammary tumors. Intl. J. Tiss. React., 12(SuppI.) :51–56, 1990. (37). Rubin, H., and Colby, C., Early release of growth inhibition in cells infected with Rous sarcoma virus. Proc. Natl. Acad. Sci. USA, 60: 752–759, 1982.

(38). Parod, S. and Brambilla, G., Relationship between mutation and transformation frequencies in mammlian cells treated in vitro with chemical carcinogens. Mutat. Res., 47:53. 1977.

(39). Liau, M. C., Lee, S. S., and Burzynski, S. R., Modulation of cancer methylation complex isozymes as a decisive factor in the induction of terminal differentiation mediated by antineoplaston A5. Intl. J. Tiss. React. 12(Suppl): 27–36, 1990b.

(40). Liau, M. C., Liau, C. P., and Burzynski, S. R., Potentiation of induced terminal differentiation by phenylacetic acid and related chemicals. Intl. J. Exptl. Clin. Chemother. 5: 9–17, 1992.

(41). Burzynski, S. R., Mohabbat, M. O., .Lee S. S., Preclinical studies in Antineoplaston AS2-1 and Antineoplaston AS2-5. Drugs Exptl. Clin.Res. 12(Suppl.I): 11–16, 1986a.

(42). Burzynski, S. R., Burzynski, B., Mohabbat, M. O., Toxicology studies in antineoplaston AS2–1injections in cancer patients. Drugs Exptl. Clin. Res., 12(Suppl. I): 25–36, 1986b.

(43). Ram, Z., Samid, D., Walbriddge, S., Oshiro, E. M., Viola, J. J., Tao-Cheng, J. H. Shack, S., Thibault, A., Myers, C. E., Oldfield E. H. Growth inhibition, tumor maturation, and extended survival in experimental brain tumors in rats treated with phenylacetate. Cancer Res., 54: 2923–2927, 1994.

(44). Adamson, P. C., Boylan, B. F., Balis, F. M., Murfy, R. F., Godwin, K. A.Gudas, L. T., and Poplack,D. G., Time course of induction of metabolism of all-trans retinoic acid and the up-regulation of cellular retinoic acid binding protein Cancer Res.,53:472–476,1993.

(45). Yen, A., Reese, S. L. and Albright, K. L., Dependence of HL-60 myeloid cell differentiation on continuous and split retinoic acid exposure: precommitment memory associated with altered nuclear structure. J. Cell Physiol., 118:277–286, 1984.

(46). Yen, A., Reese, S. L., and Albright, K. L., Control of cell differentiation during proliferation. II. Mycloid differentiation and cell cycle arrest of HL-60 promyelocytes preceded by nuclear structural changes. Leuk. Res., 9: 51–71, 1985a.

(47). Yen, A., Control of HL-60 myeloid differentiation: Evidence of uncoupled growth and differentiation, S-phase specificity, and two step regulation. Exp. Cell Res., 156: 198–212, 1985b.

(48). Burzynski, S. R., and Kubove, E., Phase I clincial studies of antineoplastons A3 injections. Drugs Exptl. Clin. Res., 13 (Suppl.1):13–30,1987b.

(49). Burzynski, S. R., Kubove, E. and Burzynski, B., Phase I clinical studies of antineoplaston A5 injections. Drug Exptl. Clin. Res., 13(Suppl.1):33–44,1987c.

(50). Burzynski, S. R., Treatment of malignant brain tumors with antineoplastons. Adv. Exp.Clin.Chemother.6/88:45–46,1988.

(51). Slobodan D., Petrovic, Nada D., Stojanovic, Ostoja K., Stojanovic, Nestor L. Kobilarox, J. Serb. Chem. Soc., 51, 395–405, 1986.

(52). Japanese patent laid-open No. 61–271250(1986).

(53). El-Chahawi, Moustafa; Richtzenhain, Hermann, Ger. Offen. 2,240,399(Cl. C 07c), 28 Feb. 1974, Appl. P22 40 399.2, 17 Aug. 1972.

What is claimed is:

1. A method of inducing terminal differentiation in cancer cells by a differentiation inducer, comprising the step of administering to said cancer cells an effective amount of a helper inducer selected from the group consisting of methyl phenylacetamide and ethyl phenylacetamide.

2. The method of claim 1, wherein said effective amount of said helper inducer is non-toxic to physiologically normal cells.

* * * * *

UNITED STATES PATENT AND TRADEMARK OFFICE
CERTIFICATE OF CORRECTION

PATENT NO. : 5,783,605
DATED : July 21, 1998
INVENTOR(S) : Kuo et al.

It is certified that error appears in the above-indentified patent and that said Letters Patent is hereby corrected as shown below:

Col. 2, line 46 "MATL$^T$" should be --MAT$^{LT}$--;

Col. 4, line 1 please insert a --.-- between acids and Both;

Col. 8, line 8 "(CDCl$_3$3. 58" should be --(CDCl3)$\delta$ --

Col. 8, line 9 "NH$^2$" should be --NH$_2$--;

Col. 8, line 27 "10.07" should be --10.07°--

Col. 8, line 40 "14" should be -- - --

Col. 9, line 23 "-OCH$_2$" should be --OCH$_2$- --;

Col. 10, line 12 "growt" should be --growth--;

Col. 11, line 60 "Iluribert" should be --Hurlbert--; and

Col. 13, line 10 please insert a --space-- between AS2-1 and injections.

Signed and Sealed this

Twelfth Day of January, 1999

Attest:

*Attesting Officer*    *Acting Commissioner of Patents and Trademarks*